United States Patent [19]

Spencer

[11] Patent Number: 5,037,395
[45] Date of Patent: Aug. 6, 1991

[54] CATHETER FOR SUPPRESSING TUNNEL INFECTION

[75] Inventor: Dudley W. C. Spencer, Wilmington, Del.

[73] Assignee: Denco, Inc., Wilmington, Del.

[21] Appl. No.: 334,490

[22] Filed: Jun. 2, 1989

[51] Int. Cl.$^5$ ............................................. A61F 7/12
[52] U.S. Cl. ................................. 604/113; 128/401; 606/27
[58] Field of Search ............... 128/349, 401, 395, 786; 604/280, 96, 20, 21, 113, 265; 600/2; 606/14, 27; 623/66

[56] References Cited

U.S. PATENT DOCUMENTS

| | | | |
|---|---|---|---|
| 3,890,977 | 6/1975 | Wilson | 604/21 |
| 4,027,393 | 6/1977 | Ellis et al. | |
| 4,411,648 | 10/1983 | Davis et al. | 604/21 |
| 4,708,136 | 11/1987 | Saito | 128/399 |
| 4,773,413 | 9/1988 | Hussein et al. | 128/399 |
| 4,776,349 | 10/1988 | Nashef et al. | 604/265 |
| 4,872,458 | 10/1989 | Kanehira | 128/401 |

FOREIGN PATENT DOCUMENTS 315982 5/1989 European Pat. Off. ............. 604/96

Primary Examiner—Edward M. Coven
Assistant Examiner—Mark S. Graham
Attorney, Agent, or Firm—Connolly & Hutz

[57] ABSTRACT

An implanted catheter suppresses tunnel infection by having its surface temperature raised to a point above which the bacteria residing on the surface cannot survive. The temperature is held at that temperature level for 20 milliseconds whereby the catheter can be cleaned of the bio-burden.

12 Claims, 2 Drawing Sheets

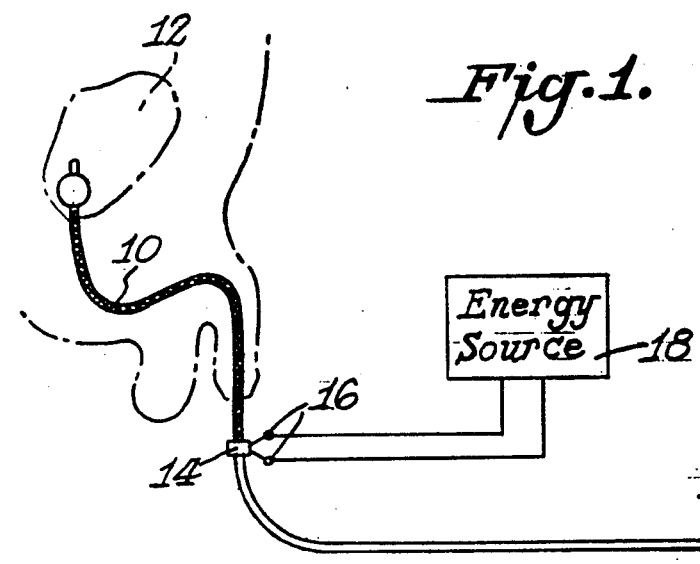
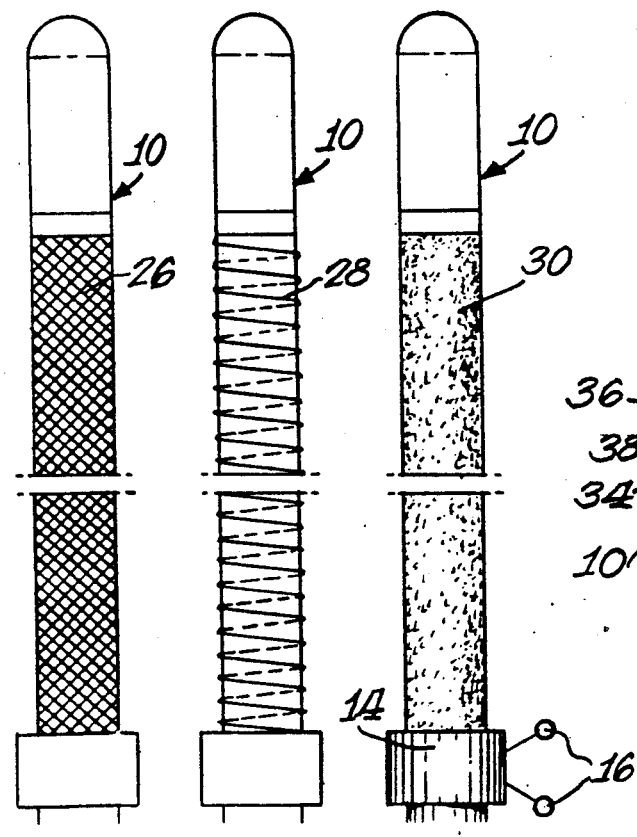
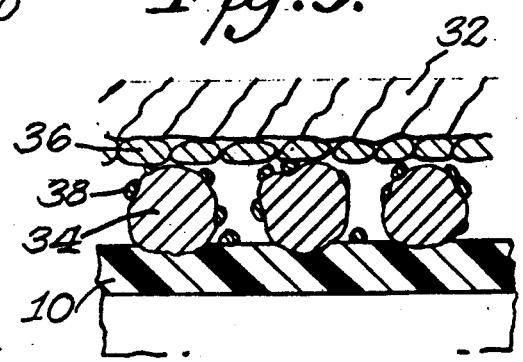

CATHETER FOR SUPPRESSING TUNNEL INFECTION

BACKGROUND OF THE INVENTION

Medical patients who have implanted catheters often experience an acute or chronic infection problem that results from bio-burden entering the body between the meatus and the catheter surface. For example, patients who have urinary drainage catheters inserted into the bladder via the urethra for post-operative therapy, or long term catheters for paraplegics can expect to develop urinary tract infections within 10 days after catheterization. Patients with implanted catheters for continuous ambulatory, peritoneal dialysis are also at risk.

Extensive studies have shown the bacteria burden along the catheter length can be multi-layered and thus resistant to antibiotics which are unable to reach the bottom and bacterium reproduction layers. It would be desirable to provide techniques for killing the bacteria on the catheter surface without deleterious effect to the patient. This treatment effectively safeguards the patient from "tunnel-infections" and their life threatening consequences.

The following attempts have been made by the prior art to reduce tunnel infections:
(1) "Goretex" bacteria seals at the epidemis;
(2) Bactericides, such as silver compounds applied to the catheter surface;
(3) Catheter replacement at frequent intervals; and
(4) Use of antibiotics (Bactrim DS).

These approaches have been marginally successful, but each has limitations that mitigate against their widespread acceptance by the medical community.

SUMMARY OF THE INVENTION

The present invention relates to a process and apparatus for killing the bio-burden that attaches to the catheter surface exterior and which is useful for both "in-vivo" and "in-vitro" applications.

By raising the surface temperature of the catheter where the bacteria reside, to a point above which the bacteria cannot survive, and holding the temperature at that level for 20 milliseconds the catheter can be cleaned of the bio-burden. The procedure when initiated will keep the catheter clear of bio-burden.

The patient will not feel the heat sensation from the treatment even though the catheter surface reaches temperatures of 500° F. because of the "Leydenfrost". Simply stated, the "Leydenfrost" phenomena is at work when one moistens ones finger to test the temperature of a hot iron. The sizzle, is the insulation effect provided by extremely fast nucleation of the residual moisture to form vapor bubbles and thus protect the skin from damage or sensation of heat.

The impressed instantaneous (e.g. 20 millisecond) burst of energy along the catheter surface is sufficient to create the "Leydenfrost" phenomena by nucleating the body fluids that intimately surround the catheter surface. This layer is sufficient to insulate the body tissue from harm, and at the same time concentrate the heat where it is most needed to kill the bacteria. The bacteria is trapped between a hot source and an insulation layer.

One of the advantages of using laser energy is the transparency of medical grade, PVC tubing to laser light.

The laser light could be piped down the tube interior via optical fibers and caused to focus at the terminal end by means of a cylindrical distributor. The light would pass through the PVC without attenuation and impinge on the metallic layer.

The metallic layer would not only stop further penetration of the laser energy into the body it would then become the "Leydenfrost" heating element.

Providing the energy by entering the catheter inside diameter, such as power leads or optical fibers represents a breach of sterility. To avoid the problem, power leads or optical fibers must enter the system using sterile connection technology as taught in U.S. Pat. Nos. 4,793,880 and 4,753,697 and a special port in the patient line.

THE DRAWINGS

FIG. 1 is an elevation view partly broken away, schematically illustrating a catheter in accordance with this invention.

FIGS. 2-4 are front elevation views of alternative catheter structures in accordance with this invention.

FIG. 5 is a cross-sectional view in elevation on an enlarged scale of a portion of a catheter mounted below the tissue of a patient.

DETAILED DESCRIPTION

Figure 6:
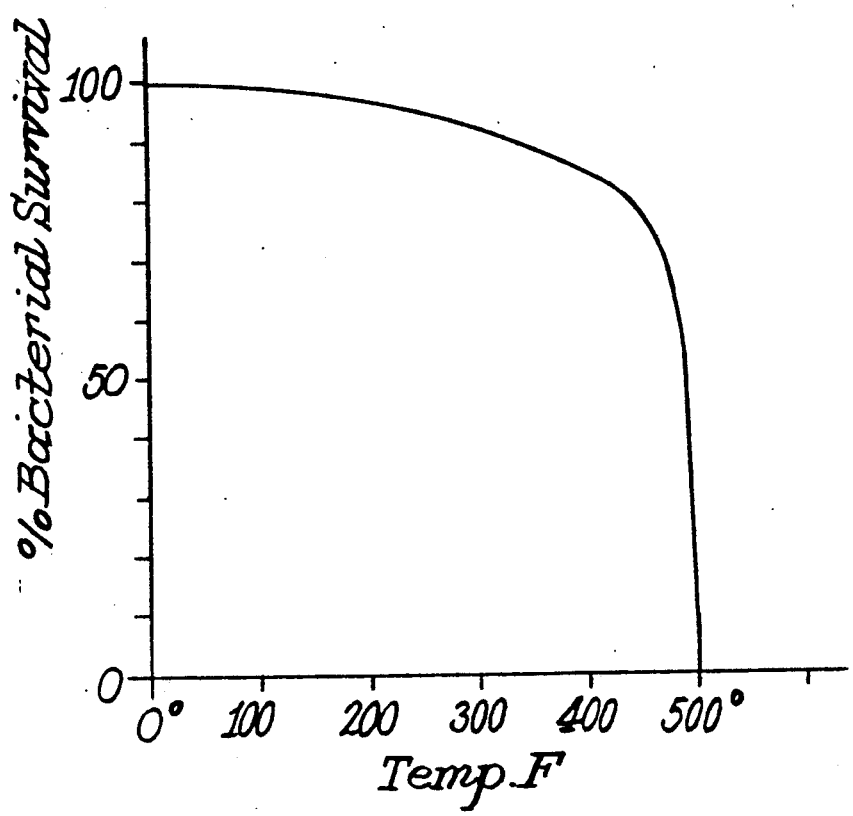
FIG. 6 is a graph illustrating the effect of bacteria survival in accordance with temperature.

FIG. 1 illustrates a practice of the invention used in association with a urinary drainage catheter. As shown therein, the catheter 10 which is illustrated as being a Foley Catheter is inserted into the bladder 12 of a patient. The catheter terminates in a cuff 14 having a pair of power contacts 16 connected to an energy source 18 for applying an instantaneous application of heat to the catheter surface. A tube 20 connects the catheter to a drainage bag 22 which collects the urine 24.

It is to be understood that although FIG. 1 illustrates catheter 10 in its application for urinary drainage, the invention may be practiced for various other applications, some of which will be described hereinafter.

FIGS. 2-4 illustrate various alternative catheter structures which includes modification of the outer surface of the catheter to enhance the growth of bacteria thereon concentrated thereon at the surface and thereby facilitate the bacteria being killed when the energy is applied to raise the surface of the catheter to a temperature above which the bacteria cannot survive with this temperature being held for a sufficient time, such as 20 milliseconds to permit the catheter to be cleaned of the bio-burden. Although the treatment temperature may be, for example, 500° F. the patient will not feel the heat sensation because of "Leydenfrost". FIG. 2 illustrates the surface treatment to include a braid structure 26 which results in an intricate pattern on which the bacteria colony would form, similar to the formation of barnacles on the rough seams of a boat hull or to coral formations on reefs. FIG. 3 illustrates an alternative arrangement wherein the intricate pattern is formed by providing a rough wire 28 wound around the outer surface of catheter 10. FIG. 4 illustrates a further embodiment in which the roughened surface 30 is formed on the outer surface of the catheter and itself without the addition of any extraneous structure.

By encouraging bacteria colony formation on the surface of the catheter, the bacteria is concentrated at a point where the bacteria can be killed with the least amount of Joule energy. The rough wire surfaces 28, for example, provide the necessary high energy sight from which bubble nucleation can be quickly generated. The rough points of the wire, in effect, create hot spots above the average wire temperature. These hot spots are responsible for the ultra-fast nucleation or the "Leydenfrost" effect.

The preferred arrangement for the outer surface of the catheter would be to vapor deposit a metal film on the tubing wall of catheter 12. Preferred materials for these resistance metals are gold, copper, platinum, silver, alum, and stainless steel. Such materials could also be used for the braid 26 and coil 28. The catheter 10 itself can be made of a wide variety of bio-compatible polymeric materials including thin metals such as stainless steel.

Any suitable means of energy source could be used. For example, the invention may be practiced by the utilization of laser energy focused on the bacteria layer. An alternative energy source could be electrical resistance or pulsed xenon flash tube (I.R. source).

FIG. 5 illustrates the "Leydenfrost" phenomena. As shown therein the catheter 10 is implanted in the patient below the meatus 32. The outer tube wall of catheter 10 would include a heater element 34 which could be in any of the previously noted forms. Insulating "Leydenfrost" 36 would form between the meatus 32 and heater element 34. The bacteria 38 would form in a trapped layer around the heater element 34 between the "Leydenfrost" and the tube wall of catheter 10. When the heat is instantaneously applied to the heater element 34 the trapped bacteria is killed.

FIG. 6 illustrates the effect of temperature on the bacterial survival. As shown therein, a dramatic decrease in bacterial survival occurs as the temperature approaches 500° F. The time frame for the graph of FIG. 6 is 20 milliseconds. Accordingly, the invention is practiced in its preferred form by raising the outer surface of the catheter 10 to 500° F. when a 20 millisecond time frame is applied.

Figure 7:
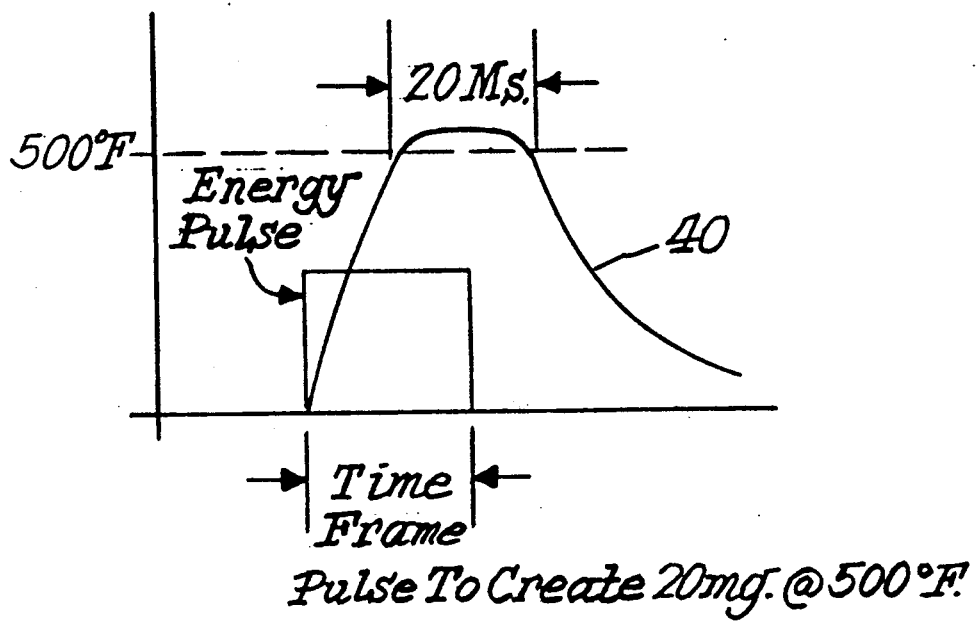
FIG. 7 is a graph illustrating the energy and temperature profiles.

FIG. 7 illustrates the energy and temperature profiles resulting from the application of energy to raise the temperature to 500° F. for the 20 millisecond time period. The energy pulse indicated therein represents the time frame of the pulse to create the 20 millisecond duration at 500° F. The temperature profile itself is illustrated by the curve 40.

The inside diameter of the tubing for catheter 10 can be entered by using external power contacts in the following manner, which is intended to be typical of what would be useful in actual practice In this example, a tube is used of a given diameter and wall thickness, typically made of a flexible plastic such as Kapton (R). The interior of the tube holds the catheter, while the outside of the tube is plated with metal, e.g. gold. On electrode is attached to each end of the tube and an electrical current pulse is sent through this coating (axial direction). The current heats the coating by Joule heat, and transfers the heat to attached bacteria and to the tubing.

The goal is to give the coating a temperature pulse of e.g. 20 ms duration in which the temperature should rise by 200K (360 deg F.). Systems limitations currently are set at a maximum voltage of 15 V, applicable metals for the coating: Au, Ag, Cu, Al, and Pd.

A typical condition that satisfies the current limits is the following. The tube diameter is 3 mm (3/16 in), length 150 mm (6 in), wall and coating thickness 100 and 8 micrometer, resp. (4 and 0.3 m-in). The coating is Au, which gives a resistance of 0.095 ohm. A 20 ms pulse at 15 V will cause a temperature rise of 175 to 1713K (300 to 3000 deg F.). The upper limit is the theoretical limit value, corresponding with an adiabatic deposition of the energy in the coating only, while the lower value assumes that the tube is heated uniformly to the coating temperature. If the pulse duration is shortened, the system will be more adiabatic and tend to the higher temperature. Longer pulses will hold down the temperature due to more heat transfer into the tubing. Using an approximated average (this can be refined at a later stage), a 12 V pulse at 20 ms will give the 200K rise.

Changing the coating from Au to other metals shows that Pd falls outside the practical range, but that the other metals could be used for the given conditions.

| Metal | Temp. range | V |
|---|---|---|
| Au | 175–1713 | 12 |
| Cu | 237–1690 | 10 |
| Pd | 37–334 | 26 |
| Ag | 263–2520 | 9.7 |
| Al | 140–1380 | 13 |

Changing the other parameters has the following effects. The Au system (top line in above Table) is used as the standard, and only one variable is adjusted at a time. Changing the coating thickness from 8 to 15 micro-meters—this is the common range of typical coatings—gives a temperature range from 300 to 1713K or an expected voltage of 9.4 V. If instead the tube length is reduced from 150 to 50 mm, the range is 1500 to 15000K, at 4 V. Finally, if the tube wall thickness is halved (100 to 50), the range is 319 to 1713K at 9.1 V average. Note that the result in this problem is independent of the tube diameter: although the current changes with diameter, the temperature range and average expected voltage remain constant.

The concepts of the invention may be practiced for accomplishing the following end uses:

(1) Can be used to pre-sterilize itself before insertion (if a sterilizer is not available).
(2) A more frequent pulse at a lower temperature will discourage bacteria entering.
(3) Could have just a ring of heat at only the entrance such as the cuff arrangement on Tenkoff catheters.
(4) Can form Leydenfrost ring (see FIG. 5).
(5) A means of sterilizing hypodermic needles for reuse.
(6) A means of sterilizing a thermometer or other invasive medical instrument.
(7) A means of sterilizing the A-V shunt used in hemodialysis.
(8) A means of making an antiseptic for skin sterilization in remote areas (e.g. battlefields) where normal antiseptics are not available or difficult to transport.
(9) A means of providing antiseptic capability to "band-aid" type patches.
(10) A means of controlling waste disposal from hazardous areas i.e. AIDS or urinary drainage ward sewer lines can contain potentially lethal bacteria.

The invention provides the following advantages:
(1) A bacteria killing process, in vivo that effectively removes the bio-burden without deleterious effect to the patient.

(2) A catheter heating means surrounding the catheter.
(3) Making use of the Leydenfrost phenomena to trap the bacteria in a killing zone.
(4) Using the Leydenfrost effect to insulate body tissue from the 20 millisecond heat impulse.
(5) Pulses of energy at a frequency great enough that bacteria cannot penetrate body.
(6) Bacteria encouraged to adhere to the killing surface.

Although the preferred practice of the invention is to raise the temperature of the catheter outer surface to 500° F. for 20 ms, the invention could be practiced with other times and temperatures. The temperature can range from 250° to 600° F. and preferably 350°–500° F. and the time range can be 10–100 ms, preferably 18–30 ms.

What is claimed is:

1. A catheter for suppressing tunnel infection comprising a tubular body made of a bio-compatible polymeric material and having an outer surface and a distal end, a metal layer on said outer surface over the major area of said outer surface without extending to said distal end of said body, said metal layer being a roughened surface for enhancing the growth of bacteria thereon, said metal layer comprising energy absorbing means capable of being raised to a temperature of at least 250° F. to kill bacteria on said outer surface, and an energy source connected at said outer surface to said energy absorbing means for providing a burst of energy to said energy absorbing means to raise the temperature thereof for a controlled period of time whereby the bacteria may be killed and a Leydenfrost effect may be created to protect the patient during the temperature rise.

2. The catheter of claim 1 including power contacts on said outer surface connecting said energy source to said energy absorbing means.

3. The catheter of claim 2 including a cuff mounted on said outer surface, and said power contacts being mounted to said cuff.

4. The catheter of claim 1 wherein said metal layer is made from a metal selected from the group consisting of gold, copper, platinum, silver, alum and stainless steel.

5. The catheter of claim 1 wherein said energy source is laser means focused on said outer surface.

6. The catheter of claim 1 wherein said energy source is a pulsed xenon flash tube.

7. The catheter of claim 2 wherein said energy source is electrical resistance means.

8. The catheter of claim 1 wherein said tubular body is made of pvc.

9. The catheter of claim 1 wherein said metal layer has a thickness of 8 micrometers.

10. The catheter of claim 1 wherein said metal layer is vapor deposited on said tubular body.

11. A catheter for suppressing tunnel infection comprising a tubular body made of a bio-compatible polymeric material and having an outer surface and a distal end, a braided metal structure on said outer surface over the major area of said outer surface without extending to said distal end of said body, said metal structure comprising means for enhancing the growth of bacteria thereon, said metal structure comprising energy absorbing means capable of being raised to a temperature of at least 250° F. to kill bacteria on said outer surface, and an energy source connected at said outer surface to said energy absorbing means for providing a burst of energy to said energy absorbing means to raise the temperature thereof for a controlled period of time whereby the bacteria may be killed and a Leydenfrost effect may be created to protect the patient during the temperature rise.

12. A catheter for suppressing tunnel infection comprising a tubular body made of a bio-compatible polymeric material and having an outer surface and a distal end, a metal coil wound around said outer surface over the major area of said outer surface without extending to said distal end of said body, said metal coil comprising means for enhancing the growth of bacteria thereon, said metal coil comprising energy absorbing means capable of being raised to a temperature of at least 250° F. to kill bacteria on said outer surface, and an energy source connected at said outer surface to said energy absorbing means for providing a burst of energy to said energy absorbing means to raise the temperature thereof for a controlled period of time whereby the bacteria may be killed and a Leydenfrost effect may be created to protect the patient during the temperature rise.

* * * * *